United States Patent [19]
Matthews et al.

[11] Patent Number: 5,273,738
[45] Date of Patent: Dec. 28, 1993

[54] RADIATION DELIVERY TO LYMPHOID AND MARROW TISSUES

[75] Inventors: Dana C. Matthews; Irwin D. Bernstein, both of Seattle; John A. Hansen, Mercer Island; Fred R. Appelbaum, Seattle; Claudio Anasetti, Seattle; Paul J. Martin, Seattle, all of Wash.

[73] Assignee: Fred Hutchinson Cancer Research Center, Seattle, Wash.

[21] Appl. No.: 562,127

[22] Filed: Mar. 3, 1990

[51] Int. Cl.$^5$ .................. A61K 43/00; A61K 49/02
[52] U.S. Cl. ............................. 424/1.1; 530/391.3
[58] Field of Search ................ 424/1.1, 9, 85.91; 530/387, 402, 391.3, 391.5

[56] References Cited

U.S. PATENT DOCUMENTS

| | | | |
|---|---|---|---|
| 4,582,797 | 4/1986 | Trowbridge | 435/68 |
| 4,626,507 | 12/1986 | Trowbridge et al. | 435/240 |
| 4,911,690 | 3/1990 | Mulshine et al. | 424/1.1 X |
| 5,002,869 | 3/1991 | Schlossman et al. | 424/1.1 |
| 5,028,424 | 7/1991 | Evans | 424/85.8 |
| 5,091,178 | 2/1992 | Hellstrom et al. | 424/85.8 |

FOREIGN PATENT DOCUMENTS

WO82/01192 4/1982 European Pat. Off. ............ 435/68

OTHER PUBLICATIONS

Nourigat, C., et al., "Treatment of Lymphoma With Radiolabeled Antibody: Elimination of Tumor Cells Lacking Target Antigen," *Journal of the National Cancer Institute* 82(1):47-50 (Jan. 1990).

Thomas, M. L., The leukocyte common antigen family, *Ann. Rev. Immunol.* 7:339-369, 1989.

Thomas, M. L. et al., Differential expression of the leucocyte-common antigen family, *Immunology Today* 9(10):320-326, 1988.

Clark, E. A. et al., Leukocyte cell surface enzymology: CD45 (LCA, T200) is a protein tyrosine phosphatase, *Immunology Today* 10(7):225-228, 1989.

Tonks, N. K. et al., Demonstration that the leukocyte common antigen CD45 is a protein tyrosine phosphatase, *Biochemistry* 27(24):8701-8706, 1988.

Shah, V. O. et al., Flow cytometric analysis of human bone marrow. IV. Differential quantitative expression of T-200 common leukocyte antigen during normal hemopoiesis, *The Journal of Immunology* 140(6):1861-1867, 1988.

Ralph, S. J. et al., Structural variants of human T200 glycoprotein (leukocyte-common antigen), *The EMBO Journal* 6(5):1251-1257, 1987.

Omary, M. B. et al., Human homologue of murine T200 glycoprotein, *J. Exp. Med.* 152:842-852, 1980.

Ledbetter, J. A. et al., CD45 regulates signal transduction and lymphocyte activation by specific association with receptor molecules on T or B cells. *Proc. Natl. Acad., Sci. USA* 85:8628-8632, 1988.

Charbonneau, H. et al., The leukocyte common antigen (CD45): A putative receptor-linked protein tyrosine phosphatase, *Proc. Natl. Acad. Sci. USA* 85:7182-7186, 1988.

McMichael, A. J. et al., Eds. Chapter 15: Non-lineage, LFA-1 family, and leucocyte common antigens, in *Leukocyte Typing III: White Cell Differentiation Antigens*, Oxford University Press, 1987.

Starling, G. C. et al., Inhibition of natural killer-cell mediated cytolysis with monoclonal antibodies to restricted and non-restricted epitopes of the leucocyte common antigen, *Immunology* 61:351-356, 1987.

(List continued on next page.)

*Primary Examiner*—Robert L. Stoll
*Assistant Examiner*—Lara E. Chapman
*Attorney, Agent, or Firm*—Christensen, O'Connor, Johnson & Kindness

[57] ABSTRACT

A method of selectively delivering radiation homogeneously to lymphoid and marrow tissues in vivo including the step of administering an effective dose of a radiolabeled immunological binding partner of a T-200 antigen to a patient is disclosed. Also disclosed are immunological binding partners and compositions based thereon for carrying out the method.

14 Claims, No Drawings

OTHER PUBLICATIONS

Tighe, H. et al., Blocking of cytotoxic T cell function by monoclonal antibodies against the CD45 antigen (T200/leukocyte-common antigen), *Transplantation* 44(6):818-823, 1987.

Andres, T. L. et al., Immunologic markers in the differential diagnosis of small round cell tumors from lymphocytic lymphoma and leukemia, *Am. J. Clin. Path.* 79(5):546-552, 1983.

Bindon, C. I. et al., Therapeutic potential of monoclonal antibodies to the leukocyte-common antigen, *Transplantation* 40(5):538-544, 1985.

Fabre, J. W. et al., Immunosuppressive properties of rabbit antibodies against a major glycoprotein restricted to rat leukocyte membranes, *Transplantation* 30(3):167-173, 1980.

Harp, J. A. et al., Modulation of in vitro immune responses by monoclonal antibody to T200 antigen, *Immunology* 81:71-80, 1983.

Ledbetter, J. A. et al., Antibodies to common leukocyte antigen p220 influence human T cell proliferation by modifying IL 2 receptor expression, *The Journal of Immunology* 135(3):1819-1825, 1985.

Martorell, J. et al., A second signal for T cell mitogenesis provided by monoclonal antibodies CD45 (T200), *Eur. J. Immunol.* 17:1447-1451, 1987.

Mittler, R. S. et al., Antibodies to the common leukocyte antigen (T200) inhibit an early phase in the activation of resting human B cells, *The Journal of Immunology* 138(10):3159-3166, 1987.

Schraven, B. et al., Triggering of the alternative pathway of human T cell activation involves members of the T200 family of glycoproteins, *Eur. J. Immunol.* 19:397-403, 1989.

Sparrow, R. L. et al., A function for human T200 in natural killer cytolysis, *Transplantation* 36(2):166-171, 1983.

Takeuchi, T. et al., Amplification of suppressor inducer pathway with monoclonal antibody, anti-2H4, identifying a novel epitope of the common leukocyte antigen/T200 antigen, *Cellular Immunology* 118:68-84, 1989.

RADIATION DELIVERY TO LYMPHOID AND MARROW TISSUES

This invention was made with government support under National Institutes of Health grant Nos. CA44991, CA26386, and CA29548 awarded by the National Institutes of Health. The government has certain rights in the invention.

FIELD OF THE INVENTION

The present invention relates to methods and compositions for use in delivering radiation homogeneously to lymphoid and marrow tissue in patients.

BACKGROUND OF THE INVENTION

Before the present invention, radiation delivery in the bone marrow transplant setting has depended upon the clinical indication. When treating marrow-based diseases by a marrow transplant, irradiation has been delivered almost solely by external beam total body irradiation (TBI). Attempts to improve the rate of eradication of malignant cells by increasing the dose of radiation delivered have generally been limited by toxicity to normal organs such as lung or liver.

Marrow transplants in which the main goal is marrow ablation (rather than eradication of a malignancy) have used either TBI with chemotherapy, or a chemotherapy-only regimen. In either case, the therapy is not delivered specifically to sites of disease, but is instead given systemically, and each type of regimen has potential toxicities to normal organs. The ability to avoid exposing the lung and liver to high doses of irradiation and/or chemotherapy, while delivering adequate doses to marrow and lymphoid tissue, would allow transplants for these conditions to be performed with less risk to the patient.

Immunosuppression in the marrow transplant setting has generally been achieved by TBI/chemotherapy, or chemotherapy-only regimens, which again have a high rate of toxicity to normal organs. In some cases, such as mismatched or T-cell depleted marrow transplants, even the usual TBI-containing regimens frequently fail to achieve adequate immunosuppression and graft rejection occurs in an unacceptably high number of patients. The delivery of additional "total lymphoid irradiation" (TLI) by directed external beam radiotherapy has increased the degree of immunosuppression but its use has been limited by toxicity to neighboring tissues, particularly the mucosa of the mouth, oropharynx, and esophagus.

In summary, although in general higher doses of irradiation have led to decreased rates of relapse and enhanced immunosuppression, this has not translated to improved survival because of the accompanying severe regimen-related toxicity when this irradiation is delivered via traditional, external beam sources (TBI or TLI).

In general, most previous reported attempts to destroy malignant or otherwise undesirable cells with a targeted "magic bullet" approach have purposefully used monoclonal antibodies which are as "tumor specific" as possible. For example, in experimental studies of radiolabeled antibody therapy of lymphoma, the present inventors have tested the theoretically most "tumor-specific" reagent possible, which is an antibody reactive with the "idiotypic determinant" which is specific to the immunoglobulin molecule expressed only by the cells of the lymphoma itself (that is, not by normal lymphocytes). Alternatively, they have tested the approach of targeting an antigen present on most B cells, including the lymphoma cells. This is, in a sense, "one step less specific" than the anti-idiotype antibodies. In this case, the selection of a pan-B reactive antibody is one of convenience, in that such an antibody reacts with most lymphomas (and therefore need not be tailor-made for each patient), yet still is relatively tumor-specific; the reactivity with normal nonlymphomatous B cells is accepted although such cells are not the primary target. Other clinical trials of targeted radiotherapy using monoclonal antibodies have also generally employed antibodies which are as tumor-specific as possible, accepting nontumor reactivity as an unavoidable side effect.

SUMMARY OF THE INVENTION

A unique aspect of the invention is that it was developed starting with an express goal of targeting neighboring normal cells as well as the malignant cells, given that it is desired to treat patients whose malignancy is in remission, as well as those in relapse. Patients in remission have, by definition, too few malignant cells to be detectable by usual clinical means. As an example, a patient with acute lymphocytic leukemia is said to be "in remission" if there are fewer than 5% of cells in the marrow that have the appearance of blast cells. In this setting, targeting only the malignant cells with radiolabeled antibody would not allow optimum delivery of radiation to such cells if they are relatively isolated and are scattered among normal cells. Since the radioactivity from the isotope on an antibody molecule bound to a cell can be emitted in any direction, only a small percentage of the radioactivity from antibodies bound to any one cell will be delivered to that cell; thus, a very high number of bound antibody molecules will be required to mediate delivery of adequate irradiation to cause cell death. Such isolated cells would be much more likely to be lethally irradiated if the surrounding cells are also bound by radiolabeled antibody, and a lower average number of antibody molecules bound per cell will be required. This approach further allows killing of malignant cells which may not express the target antigen, providing they are surrounded by a significant number of cells which do.

This concept led to selection herein of the T200 (CD45) antigen as a target for radiolabeled immunological binding partner (e.g., antibody) therapy. This differs from the approach used by others particularly because it is the most widely distributed hematopoietic antigen and therefore the least specific potential target for treatment of hematopoietic malignancies. Because the T200 antigen is widely distributed, being present on virtually all circulating white blood cells and on reticuloendothelial cells in lung and liver, one acquainted with the known distribution of this antigen would predict that a radiolabeled anti-T200 monoclonal antibody would probably result in fairly nonspecific delivery of radiation when administered in vivo; that is, that both the binding of the antibody to resident macrophages in liver and lung, as well as the pooling of circulating, antibody-coated leukocytes in these organs would result in the delivery of unacceptably high doses of irradiation to these critical normal organs, thus limiting the therapeutic ratio achievable. An unprecedented and unpredictable aspect of the observed results reported herein was the high therapeutic ratio achieved in preliminary studies of the biodistribution of anti-T200 antibodies in a primate, as can be seen in the Examples Section herein, particularly in Tables 1-3. Although there is demonstrable binding of the monoclonal antibody to liver and lung (i.e., levels of the specific antibody that are greater than that of the negative control antibody), the very high levels achievable in the combined target tissues of marrow, lymph nodes and spleen are several fold higher than even the highest level in liver, kidney, or lung. Further, analysis of targeted cells in nodes, spleen and marrow has shown that the cells which express the antigen can be saturated with the administered antibody. Therefore, the goal of delivery of irradiation to these sites where cells of hematopoietic malignancy reside is achievable with relatively low, and certainly acceptable, irradiation to critical normal organs.

DETAILED DISCLOSURE OF THE INVENTION

The present invention provides methods and reagents for selectively delivering radiation to a patient. By "selectively" is meant that the radiation is delivered at higher levels to lymphoid and marrow tissues (e.g., lymph nodes and spleen) than to other tissues (e.g., liver and lung). For example, in vivo testing with radiolabeled antibodies against a T-200 antigen has surprisingly revealed that at least approximately 3-5 fold more radiation may be delivered to the combination of spleen, lymph nodes, and bone marrow than to liver, kidney, or lung.

A convenient way of expressing selectivity in the present context is by way of a therapeutic ratio. As used herein "therapeutic ratio" means the ratio of irradiation received by target tissues to that received by the critical normal organ receiving the highest dose. Preferably, the therapeutic ratio of the compositions disclosed herein will be greater than 1, more preferably from about 3 to about 5. This compares with therapeutic ratios of essentially 1 that are achieved with available current treatment regimens that do not deliver irradiation specifically to target tissue.

In general, the selectivity of radiation delivery in vivo, after administration of the radiolabeled immunological binding partners discussed herein may be determined by carrying out conventional biodistribution measurements after a desirable time period, conveniently from 1 to 48 hours or more after administration of an immunological binding partner (IBP) such as an antibody. A preferred method of measuring biodistribution of radiation and, hence, selectivity is described in detail in the Examples section.

For in vivo preclinical biodistribution determination, absolute values of percent injected dose per gram of tissue are obtained for both target tissues (nodes, spleen, and less reliably, marrow) and normal organs (such as liver and lung). We then work "backwards" from these known values, correlating the gamma camera images from the same time point, and generate time-activity curves using the earlier gamma camera images. Dosimetry is then estimated from these curves and the weight of the various organs.

In clinical studies with patients, absolute values are not obtained for all tissues. Instead, estimates of percent dose delivered to organs are generated directly from the gamma camera images using organ volumes obtained from CT scans, and calibrating gamma camera counts to controls of known radioactivity. Of the organs targeted by T-200 IBPs, the spleen would likely be most easily imaged in such a way that would allow reliable dosimetry estimates, that could then be compared to estimated dosimetry for liver, lung, and kidney to determine therapeutic ratio and "specificity." Nodes are often too small to be easily imaged. Although marrow is easily imaged by gamma camera, definite marrow dosimetry is the most difficult to estimate and would therefore be less helpful than spleen when trying to demonstrate specificity of irradiation delivery, requiring marrow biopsy to determine absolute percent injected dose per gram.

The present invention also enables delivery of radiation homogeneously throughout the targeted tissues. By "homogeneous" is meant that the radiation is delivered in substantially equal amounts throughout the targeted lymphoid and marrow tissues. Homogeneity of radiation delivery may be detected by conventional in vivo radiation detection and measurement techniques. For example, gamma camera images may be employed. Homogeneity is often determined qualitatively by visual inspection of images: however, gamma camera resolution is 1 cm or greater with $^{131}$I, so homogeneity estimates are at best crude.

Herein, the in vivo primate data is convincing: (1) autoradiography of thin sections of nodes and spleen show quite homogeneous distribution of isotope, and (2) Fluorescein-Activated Cell Sorter (FACS) analysis of cell suspensions from nodes, spleen and marrow demonstrates the presence of bound antibody on essentially all cells expressing the target antigen, which is virtually a saturating amount at high antibody doses.

The T200 antigen (described in greater detail hereinbelow) is expressed on all circulating leukocytes, all lymphocytes, and both myeloid and lymphoid precursors in the marrow. It is not expressed on erythrocytes or their immediate precursors, on platelets, or on megakaryocytes. Thus, a T-200 IBP targets essentially all cells in lymph nodes and other lymphoid tissue (such as tonsils) and all nonerythroid cells in the spleen. As the majority of the marrow space is devoted to myeloid cells (the usual myeloid to erythroid ratio in the marrow being 2-3:1), a T-200 IBP would thus target more than two-thirds of the cells in the marrow space. The T200 antigen is expressed on virtually all lymphomas, and the majority of acute and chronic leukemias (both myeloid and lymphoid).

The immunological binding partners (described in greater detail hereinbelow) may be administered by any conventional method suitable for delivery of radiolabeled protein/peptide materials. The preferred method is by injection. Injection may be carried out intravenously, intraarterially, and the like.

Intramuscular or subcutaneous administration of T-200 IBPs would most likely not be desirable; these routes would result in at best very delayed absorption into the circulation, delivering an unacceptably high dose of irradiation to the site of injection and impeding access of the T-200 IBP to the target tissues. The preferred method of administration would be intravenous; the length of the infusion would be determined by the dose to be administered, and in some cases, the rate-related side effects such as those seen with the administration of murine antibodies.

The effective dose of the T-200 IBP's to be used for a given patient will generally be determined by the attending physician, taking into consideration the nature of the condition to be treated and/or the result to be achieved, the body weight of the patient, the severity of the condition, the general condition of the patient, etc. Generally, the dose should be sufficient to achieve the desired selectivity of radiation delivery to and throughout the targeted tissues. A representative dose of the T-200 IBP's for this purpose will generally range from about 0.1 to about 10 mg/kg body weight of the patient.

As noted above, the effective dose of the T-200 IBP is likely to vary with the condition treated, depending on the total body "load" of cells expressing the T-200 antigen. Thus, a patient with acute leukemia in relapse whose marrow is "packed" with leukemia blasts and who has a large spleen is likely to require a larger dose (approximately 1-10 mg/kg) to achieve an acceptable therapeutic ratio than is a patient in remission, who may have less than half as many total cells to bind the T-200 IBP. This patient, or others with "normal" marrow, may need 0.1-2 mg/kg (estimate) if the T-200 IBP is intact antibody. Note that these estimated doses refer to whole antibody; the dose required of an antibody fragment (e.g., an Fab) may be smaller, for the same condition, when expressed as mg/kg because one milligram of antibody fragments contains more molecules (i.e., individual T200 IBP's) than one milligram of whole (intact) antibody. Conversely, as the smaller antibody fragments may be cleared more quickly from the body, a greater number of total molecules may be required to achieve the same degree of saturation of T-200 antigens than is needed with the intact antibody molecule.

The "dose of antibody" required does not have the same meaning as the "dose of radioactive isotope" required. The dose of antibody should be selected to provide the most optimum therapeutic ratio, which ideally is determined for each patient with a trace-labeled "dosimetry" infusion prior to the actual therapeutic dose. Once the optimum dose of antibody is established, the radiation dose is then determined depending on the situation, and manipulated by changing the number of millicuries of isotope with which that antibody dose is labeled. Thus, a patient who is also to receive TBI would receive the selected dose of antibody, labeled with the amount of isotope estimated to deliver "X" cGy to the normal organ (usually liver, lung, or kidney) receiving the highest dose of irradiation. A patient to be treated solely with radiolabeled T-200 IBP may receive a far higher dose of irradiation, by labeling the same dose of antibody with several fold more millicuries of isotope.

The T-200 IBPs of the present invention may be labeled with one or several radioactive atoms, with or without chemical ligand groups, that are compatible with whole body irradiation or radiotherapy. Specific nonlimiting examples are radioisotopes of: iodine (e.g., $^{131}$I), bromine (e.g., $^{75}$Br, $^{76}$Br and $^{77}$Br), fluorine (e.g., $^{18}$F), astatine (e.g., $^{211}$At), samarium (e.g., $^{153}$Sm), holmium (e.g., $^{150-164, 166-170}$Ho), rhenium (e.g. $^{181-184, 186-189}$Rh), and yttrium (e.g., $^{90}$Y).

Preferably, the IBP will be labeled with 1-10 radioisotope atoms, particularly preferably 1-5.

While important advances are being made in developing the technology for other radiolabels for monoclonal antibodies, it is believed that $^{131}$I is the best starting place for labeling new proteins. Iodination is always technically achievable using routine procedures (chloramine-T, iodogen), and the product can be purified by standard techniques, then evaluated for immunointegrity. A further important advantage of $^{131}$I is that the same isotope is used in both the imaging studies and the therapeutic trials—not the case for chelate labels. Because of this, dosimetric calculations derived from the preliminary imaging studies will be valid for estimating the subsequent radiation effects of various therapeutic doses. The beta particle emission of $^{131}$I is a very appropriate therapeutic agent, since its range in tissues is up to several millimeters and certain nonhomogeneous deposition of antibody at the cellular level is to be expected.

Also contemplated are chemical ligand groups that are made up of more than one atom (e.g., —R—X*, where R is a linking group such as an alkyl or substituted alkyl chain, at least one of which is radioactive (e.g., $C_1$-$C_{20}$), and X* is a radioisotope such as one of those listed above). These are referred to herein as radioactive groups. Examples are: $^{90}$Y-DTPA $^{131}$I-TCB (tyramine cellobiose), $^{131}$I-PIP (paraiodophenyl), and $^{186}$Rh-$N_2S_2$. The particular radioisotopes which would be preferable initially for use are $^{131}$I and $^{90}$Y. $^{131}$I is easy to label and can label antibody to a high specific activity. Its beta particle is of medium energy, and its photon characteristics allow it to be imaged readily. $^{90}$Y-DTPA is a well known chelate which is easy to use; the chelate has high tumor uptake and the beta particle is of medium high energy. Either of these radioisotopes require that the IBP be labeled just prior to use, to minimize damage to the IBP from the radioactivity; this would essentially be true of any radioisotope.

The radioactive atoms will be covalently bound (as with $^{131}$I) to the T-200 IBP or will be bound via chelate to the T-200 IBP. However, it is also possible to label the T-200 IBP with a binding partner group such as biotin or avidin and add one or more radiolabeled avidin or biotin molecules, respectively, to the T-200 IBP prior to administration [or even possibly after administration] to attach the radioactive label to the IBP.

Any standard method for radiolabeling of proteins/peptides can be employed to attach the radioactive group(s) to the IBP. One such method is exemplified hereinbelow.

The IBP will generally be an antibody or a fragment thereof that binds to a T-200 antigen (defined herein). Examples of suitable IBPs are monoclonal and polyclonal antibodies against a T-200 antigen or epitope-containing fragment thereof, and Fab and other binding fragments of these monoclonal and polyclonal antibodies.

Especially preferred IBP's are monoclonal antibodies reactive with a T-200 antigen. These monoclonal antibodies are typically secreted by hybridomas that may be conveniently prepared by standard techniques. For example, monoclonal antibodies that bind to T-200 antigens are described in Trowbridge, U.S. Pat. No. 4,582,797. Immunological binding partners, specific for the T-200 antigen, synthesized by recombinant DNA engineered prokaryotic or eukaryotic hosts (e.g., *E. coli, S. cerevisiae*, and COS-1 cells), are also suitable for practicing the invention.

Both murine and human hybridomas are contemplated; however, murine hybridomas are presently preferred due to greater ease in their preparation. The antibodies produced by murine hybridomas react with human T-200 antigens and so may be used in human patients.

Preferred monoclonal antibodies for use in conjunction with the present invention are the antibodies produced by the hybridoma cell lines BC8 and 9.4. Samples of these hybridoma cell lines have been deposited before the filing date herein at the American Type Culture Collection, 12301 Parklawn Drive, Rockville, Md.

20852, U.S.A., and have been accorded the accession numbers HB10507 (BC8) and HB10508 (9.4).

It is of interest to note that the antibodies produced by cell line 9.4 have a higher avidity toward the T-200 antigen expressed by human cells (approximately $5 \times 10^9 M^{-1}$) than the antibodies produced by cell line BC8 (approximately $5 \times 10^8 M^{-1}$). Unexpectedly, in macaque pre-clinical work, the use of the radiolabeled lower-avidity BC8 antibodies produces a more homogeneous distribution of radiation, e.g., in lymph nodes, than the higher avidity AC8 antibody. Accordingly, it may be preferred to employ IBP's having moderate avidity towards the T-200 antigen (i.e., about $1 \times 10^8 - 1 \times 10^9 M^{-1}$), rather than those having high avidity (i.e., $>1 \times 10^9 M^{-1}$), under circumstances where a high degree of homogeneity of radiation distribution is critical.

By "T-200 antigen" is meant a family of glycoproteins that are selectively expressed by hematopoietic cells. The family of glycoproteins has a molecular weight that generally ranges from about 180 kD to 220 kD, as determined by sodium dodecyl sulfate polyacrylamide gel electrophoresis (SDS-PAGE). The T-200 antigens are also referred to in the scientific literature as CD45 or leukocyte common antigens. They are expressed on virtually all hematopoietic cells except erythroid precursors, mature erythrocytes, and platelets. The IBPs against T-200 of the present invention preferably bind to an epitope common to all isoforms and therefore react with all lymphocytes, circulating leukocytes, and the majority of cells in the marrow. Despite this broad reactivity, T-200 does not appear to be expressed on any nonhematopoietic cells. Also, virtually all hematopoietic malignancies express the T-200 antigen.

Generally, an intact T-200 antigen (murine or human) or mixture of antigens (preferably still associated with the native lymphocyte) will be used as the immunogen in a host to prepare immunized spleen cells for fusion and selection, again typically using the T-200 antigen, resulting in the production and isolation of hybridoma cells expressing monoclonal antibodies that bind to T-200 antigens. Smaller fragments containing an epitope region of a T-200 antigen could also be used as the immunogen.

The patients that may be treated by administration of the radiolabeled immunological binding partners of the present invention are generally those patients that a physician has determined to be suffering from a condition that is treatable by radiotherapy of hematopoietic cells. The subject treatment is particularly useful as an adunct to whole body irradiation. The following disclosure details some representative situations in which the radiolabeled immunological binding partners could be used.

A. Treatment of Diseases
  1. Acute lymphocytic leukemia
  2. Acute myeloid leukemia
  3. Chromic myelogenous leukemia
  4. Non-Hodgkin's lymphoma
  5. Hodgkin's disease
  6. Myeloma and chronic lymphocytic leukemia B. Marrow Ablation
  1. Thalassemia
  2. Sickle cell anemia C. Immunosuppression
  1. Immunosuppression prior to allogeneic or autologous marrow transplantation Both human and animal patients may be treated in accordance with the present invention.

By "ablation" is meant the delivery of sufficient irradiation to the marrow space to destroy all preexisting hematopoietic cells, thereby resulting in the clearance of these cells from the space, allowing for successful engraftment of donor hematopoietic cells.

By "immunosuppression" is meant the impairment of the ability of the patient's immune system to respond to either (a) foreign antigens such as those present on HLA mismatched marrow; or (b) self antigens, when such response is inappropriate, as in autoimmune diseases.

By "allogeneic" is meant that the donor marrow is that of another individual who is not an identical twin of the recipient.

The likely protocol would include the following steps:
  (1) radiolabled antibody administration, then
  (2) chemotherapy, then
  (3) whole body irradiation (TBI) in about 200 rad doses $\times$ around 6 days, then
  (4) transporting allogeneic or autologous marrow into the patient.

Radiolabeled antibody would be given first to allow enough time for it to be adequately cleared from the patient's body prior to administration of donor marrow (to avoid irradiating the new marrow). Physiologically acceptable aqueous media would be such as 0.9% saline with or without 5% human albumin. T-200 IBP could at some point be lyophilized but would need to be reconstituted prior to labeling and labeled product would be administered in a physiologically acceptable aqueous media.

The invention now being generally described, the same will be better understood by reference to certain specific examples, which are intended to help teach one of ordinary skill in the art how to make and use the invention, and are not intended to be limiting of the present invention.

EXAMPLES

I. Methods of $^{131}$I Labeling (a) Diagnostic Doses (5-10 mCi range)

Using labeling grade $^{131}$I, we plan to iodinate the antibodies in the leadshielded shipping vial by the chloramine-T method, in which electrophilic iodination of antibody tyrosyl residues is mediated through chloramine-T in 0.05M phosphate buffered saline. The reaction is allowed to progress for 5 minutes, then is quenched by the addition of a reducing agent, sodium thiosulfate, and carrier sodium iodide. Separation of the labeled antibody product from reactants is achieved by passage of the reaction mixture over a Sephadex G-10 column previously washed with 10 column volumes of sterile isotonic saline. The fractions containing the labeled antibody are combined, passed through a 0.22 micron filter, and aliquotted for quality control testing and patient infusion. The $^{125}$I labeling of control antibody projects may be done using the same procedures as above.

B. Therapeutic Doses (100-plus mCi range)

Antibodies for therapy will be labeled by a method for high specific activity developed in our laboratory. The various components of our remote radioiodination apparatus include the $^{131}$I shipping vial, which becomes the reaction vial, a needle block carrying two stainless steel spinal needles, a charcoal trap which is vented to atmosphere inside the stainless steel fume hood, an eluant reservoir filled with 0.05M phosphate buffered saline suitable for human injection, a Sephadex G-10 purification column, a 2-channel peristaltic pump, a radiation detector, a series of four electrically driven Teflon valves, and a 0.22 μm filter for product sterilization. The entire apparatus is shielded with 3" of leaded glass plus 4" of lead bricks inside a stainless steel fume hood. Remote controls for the valves and pumps are located outside of the hood.

The reaction takes place in the shipping vial which contains reductant-free high specific activity $^{131}$I. The chloramine-T labeling reagents are introduced into the shipping vial through stainless steel needles connected to the reagent inlet line. After mechanical agitation for 5 minutes, the reaction is terminated by the addition of a $Na_2S_2O_3$ quenching mixture through the same needle. Iodine vapors that develop during agitation are vented through the charcoal trap. Passage of the reaction mixture over a Sephadex G-10 column occurs when inlet valves are rotated and a peristaltic pump transfers the mixture from the vial to the top of the column. After the transfer is complete, valves are rotated once more to direct sterile eluant from the reservoir to the column. The fractions eluting from the column that contain labeled antibody are detected by a radiation monitor and can be collected by rotating a valve to send the antibody eluant through the sterilization filter, into the radiopharmaceutical product vial. Nonproduct is passed into a waste vial. After all waste products have been eluted from the column, the entire system is eluted with the buffer, then filled with 0.1% sodium azide solution. The system remains sterile and pyrogen-free for six months or more.

In one year, 4.2 Curies of $^{131}$I were used in this apparatus for antibody labeling, with a total radiation dose to labeling personnel of only 210 mrem to whole body and 880 mrem to hands.

C. Evaluation of the Final Product

The Limulus amebocyte lysate (LAL) test is used to test a 1:10 dilution of the product for the absence of pyrogens. A similar sample is sent to the clinical microbiology laboratory for sterility testing. The immunoreactivity of the labeled antibody is evaluated by tests of binding to antigen that have been developed for each antibody being used. The basic principle of the tests include incubation of the product with the antigen, followed by separation of bound and free radioactivity. The immunoreactivity will be tested and will be expressed as percent bound radioactivity. The final product will maintain 80% or greater of its binding capacity. The expected binding capacity has been set previously for each antibody.

Radiochemical quality is checked by cellulose acetate electrophoresis. In this system, we use a barbital buffer pH 8. The labeled protein remains at the origin, and the small molecular weight reactants travel with the solvent front. By our methods, the radiochemical purity is routinely >98%. Each product will also be evaluated by HPLC using a TSK column to measure molecular weight profile and a hydroxyapatite column to test for nonspecific oxidative side reactions during iodination. If the products show extensive radiochemical inhomogeneity by these two HPLC methods, additional preparative chromatography may be required to obtain the best possible radiolabeled antibody.

II. Results obtained in a Primate Model

We have studied the biodistribution of trace $^{131}$I-labeled BC8 and a second murine monoclonal antibody reactive with the T-200 antigen, AC8, in a primate model. In this model, 5 normal preadult *Macaca nemestrina* male animals were injected with 0.5 mg/kg $^{131}$I-labeled BC8 or AC8 and at the same time were injected with an equal amount of $^{125}$I-labeled DT or 1A14 antibodies, which are isotype-matched irrelevant antibodies serving as a control. All animals tolerated the infusions well. The animals were then followed for between 48 and 96 hours, with serial scans, complete blood counts, node and marrow biopsies, followed by sacrifice for sampling of all tissues. Time-activity curves were generated for organs of interest, and the doses to these organs from the activity in the various source organs was estimated from scaling the specific absorbed fractions given in "Specific Absorbed Fractions of Energy at Various Ages from Internal Photon Sources", Cristy M., Eckerman K., ORNL/TM-8381, Oak Ridge National Laboratory, Oak Ridge, Tenn., 1987, and are presented below (for 0.5 mg/kg BC8 and AC8) as rad/millicurie when delivered as $^{131}$I-labeled monoclonal antibody.

TABLE 1

Dosimetry Estimate in Macaques: Anti-T-200 Antibodies rad/millicurie $^{131}$I-BC8 (0.5 mg/kg in Macaque)

| Organ | Average | Stand Dev |
|---|---|---|
| Marrow | 56.5 | 31.4 |
| Lymph node | 126.0 | 36.5 |
| Spleen | 174.3 | 52.0 |
| Liver | 19.8 | 4.8 |
| Kidney | 11.9 | 2.3 |
| Lung | 25.2 | 9.0 |

TABLE 2 rad/millicurie $^{131}$I-AC8 (0.5 mg/kg Macaque)

| Organ | Average | Stand Dev |
|---|---|---|
| Marrow | 66.4 | 22.2 |
| Lymph node | 40.8 | 2.3 |
| Spleen | 232.0 | 67.9 |
| Liver | 24.7 | 9.8 |
| Kidney | 8.1 | 3.6 |
| Lung | 25.8 | 14.8 |

As can be seen, the two anti-T-200 antibodies produce somewhat different dosimetry results. These antibodies differ in isotype (BC8 is an IgG1, AC8 is an IgG2a), but the isotype-matched negative control antibodies do not differ with respect to serum clearance. Their main difference is in avidity:

TABLE 3

| Antibody | Species | Avidity ($M^{-1}$) |
|---|---|---|
| BC8 | Macaque | $6 \times 10^7$ |
| BC8 | Humans | $5 \times 10^8$ |
| AC8 | Macaque | $5 \times 10^8$ |
| AC8 | Humans | nonreactive |

Therefore, the avidity of AC8 in the macaque is the same as BC8 in humans, suggesting that the dosimetry achievable with AC8 in the macaque may be most predictive of dosimetry achievable with BC8 in humans. As shown in Table 2, almost three times more irradiation is delivered to marrow than to the normal organ receiving the most irradiation (here, liver and lung receive approximately equal doses).

The data presented above demonstrates the therapeutic ratio that may be achieved using the compositions and protocols of the present invention. Based on the data, it can be seen that the therapeutic ratio, as defined hereinabove, ranges from about 1.6 to about 2.3. This is superior to either the predicted result or to prior protocols.

The examples described above are merely exemplary of various aspects of the present invention. Variations in the actual processes described in the examples will be apparent to those skilled in the art. It is therefore intended that the protection granted by Letters Patent hereon be limited only by the appended claims and equivalents thereof.

The embodiments of the invention in which an exclusive property or privilege is claimed are defined as follows:

1. A method of selectively delivering radiation homogenously to lymphoid and marrow tissues in vivo, comprising:
    administering to a patient an effective dose of a radiolabeled immunological binding partner consisting essentially of an antigen-binding site capable of binding to a T-200 antigen, wherein said effective dose results in a selective delivery of more radioactivity to bone marrow tissue than to liver or lung tissue at about 48 hours after said administering.

2. The method according to claim 1, wherein the immunological binding partner is a monoclonal antibody against a T-200 antigen.

3. The method according to claim 2, wherein said monoclonal antibody is murine.

4. The method according to claim 1, wherein said T-200 antigen is a member of a family of membrane glycoproteins having a molecular weight ranging from about 180 kD to about 220 kD as determined by SDS-PAGE, said antigen being expressed on substantially all hematopoietic cells except erythroid precursors, mature erythrocytes, and platelets.

5. The method according to claim 1, wherein said immunological binding partner is radiolabeled with a radioisotope of iodine, bromine, fluorine, astatine, samarium, rhenium, holmium, or yttrium.

6. The method according to claim 5, wherein the immunological binding partner is radiolabeled with $^{131}$I.

7. The method according to claim 1, wherein said effective dose ranges from about 0.1 mg/kg body weight to about 10 mg/kg body weight of said patient.

8. The method of claim 1, wherein said administering results in a selective delivery of at least about 2 fold more radioactivity to spleen and lymph node tissue than to liver and lung tissue at about 48 hours after said administering.

9. The method according to claim 1, wherein said patient is a human.

10. The method according to claim 1, wherein said patient has a bone marrow disease.

11. The method according to claim 1, wherein said patient has at least one of acute lymphocytic leukemia, acute myeloid leukemia, chronic myelogenous leukemia, non-Hodgkin's lymphoma, Hodgkin's disease, myeloma, or chronic lymphocytic leukemia.

12. The method according to claim 1, wherein said patient is in need of a marrow transplant.

13. The method according to claim 1, wherein said patient has a hematologic malignancy.

14. The method according to claim 1, wherein said immunological binding partner is a monoclonal antibody, or antigen-binding site thereof, produced by a hybridoma having the identifying characteristics of BC8 or 9.4, which are deposited at the ATCC under accession numbers HB10507 (BC8) and HB10508 (9.4).

* * * * *

UNITED STATES PATENT AND TRADEMARK OFFICE
CERTIFICATE OF CORRECTION

PATENT NO. : 5,273,738
DATED : December 28, 1993
INVENTOR(S) : D. C. Matthews et al.

It is certified that error appears in the above-indentified patent and that said Letters Patent is hereby corrected as shown below:

| COLUMN | LINE | |
|---|---|---|
| 5 | 56 | "(e.g. $^{181-184, 186-189}$Rh)" should read --(e.g. $^{181-184, 186-189}$Rh)-- |
| 7 | 52 | "adunct" should read --adjunct-- |
| 8 | 19 | "radiolabled" should read --radiolabeled-- |
| 11 (Claim 1 | 21 Line 2) | "homogenously" should read --homogeneously-- |

Signed and Sealed this

Twenty-fourth Day of May, 1994

Attest:

BRUCE LEHMAN

*Attesting Officer*     *Commissioner of Patents and Trademarks*